United States Patent [19]

Braunschweiler et al.

[11] Patent Number: 5,484,444
[45] Date of Patent: Jan. 16, 1996

[54] DEVICE FOR THE IMPLANTATION OF SELF-EXPANDING ENDOPROSTHESES

[75] Inventors: Reto Braunschweiler, Winterthur; Michel Bachmann, Romanel, both of Switzerland

[73] Assignee: Schneider (Europe) A.G., Bulach, Switzerland

[21] Appl. No.: 137,676

[22] Filed: Oct. 14, 1993

[30] Foreign Application Priority Data

Oct. 31, 1992 [EP] European Pat. Off. ............ 9211867

[51] Int. Cl.$^6$ ...................... A61B 19/00; A61M 25/00
[52] U.S. Cl. ...................... 606/108; 606/151; 606/191; 623/1
[58] Field of Search .................... 623/1, 11, 12, 623/900; 606/1, 108, 151, 190–198

[56] References Cited

U.S. PATENT DOCUMENTS

| | | | |
|---|---|---|---|
| 4,572,186 | 2/1986 | Gould et al. | 606/108 |
| 4,580,568 | 4/1986 | Gianturco . | |
| 4,665,918 | 5/1987 | Garza et al. . | |
| 4,681,110 | 7/1987 | Wiktor . | |
| 4,732,152 | 3/1988 | Wallsten et al. . | |
| 4,768,507 | 9/1988 | Fischell et al. . | |
| 4,875,480 | 10/1989 | Imbert . | |
| 5,026,377 | 6/1991 | Burton et al. . | |
| 5,037,427 | 8/1991 | Harada et al. | 606/108 |
| 5,201,757 | 4/1993 | Heyn et al. | 606/198 |
| 5,234,457 | 8/1993 | Andersen | 606/108 |
| 5,290,295 | 3/1994 | Querals et al. | 623/1 |

FOREIGN PATENT DOCUMENTS

| | | |
|---|---|---|
| 0416662 | 3/1991 | European Pat. Off. . |
| 0418677 | 3/1991 | European Pat. Off. . |

*Primary Examiner*—Stephen C. Pellegrino
*Assistant Examiner*—Glenn Dawson
*Attorney, Agent, or Firm*—Peter C. Richardson; Lawrence C. Akers; Philip C. Strassburger

[57] ABSTRACT

A device for implanting endoprostheses has a tubular outer body and an elongated core element placed inside of the outer body. To operate the device, both the core element and the tubular body are provided with handles at their proximal ends. In order to produce a form-locking connection between the endoprosthesis and the core element, the core element exhibits a region in which is impressed a stamping corresponding to the inner form of the endoprosthesis. As a result, there are a great number of form-locking meshing sites between the enclosed, folded endoprosthesis and the core element. A device with this type of design permits a partially released endoprostheses to be folded back up in a radially contracted state again by pushing the tubular body forward so that the endoprosthesis may be repositioned. In addition, sure and reliable operation is achieved by this type of stamping of the core element.

14 Claims, 2 Drawing Sheets

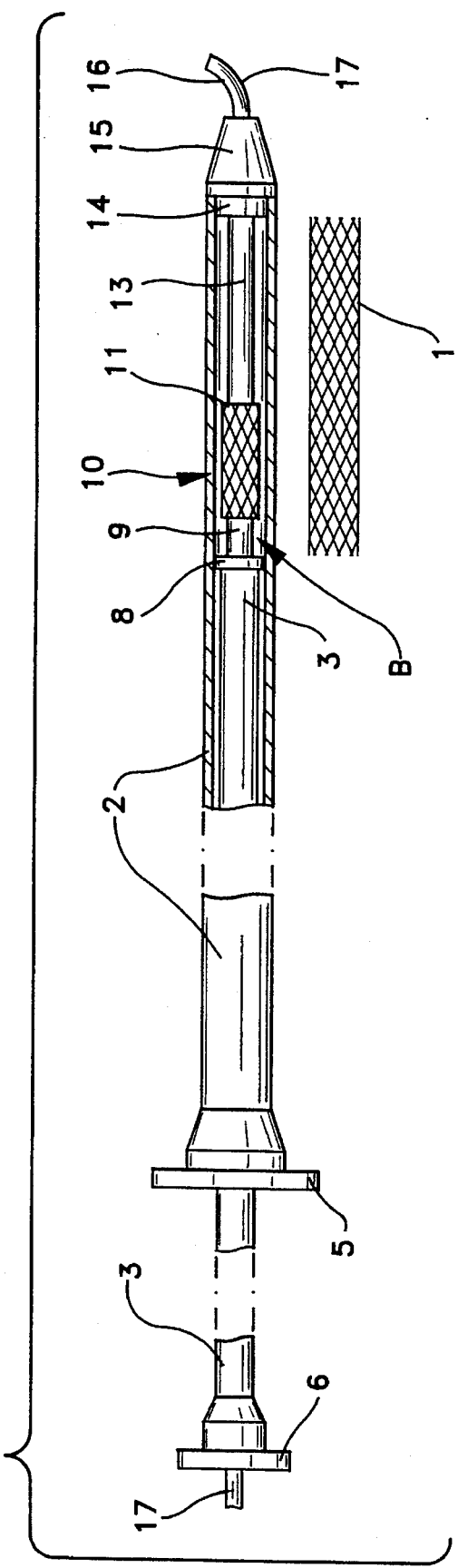

DEVICE FOR THE IMPLANTATION OF SELF-EXPANDING ENDOPROSTHESES

BACKGROUND OF THE INVENTION

The invention relates to a device for implanting self-expanding endoprostheses. Endoprostheses of the generic type can be inserted, for example, in veins, bile ducts or urinary tracts to maintain patency. They are also used to prevent recurring stenoses in the sense of an elastic recoiling or a cicatrized constriction following balloon dilation of arteries.

In most known devices, the axial length of the endoprosthesis is considerably longer when it is folded up than when it is expanded. Therefore, positioning in vessels, etc., is relatively difficult, since the exact length and location of the endoprosthesis is not apparent until after it unfolds. In most known devices, the endoprostheses can be released by way of a relative motion between the tubular body and the core element.

A common feature of all the devices currently available on the market, however, is the fact that once the endoprosthesis is partially released, it can no longer be folded back up again. This means that once even just a small piece of the endoprosthesis is released, the device can only be removed from the body by completely releasing the endoprosthesis and leaving it in the body. Moreover, once the endoprosthesis is partially released, it can only be pulled proximally but not pushed, since the expanded distal end of the endoprosthesis would inevitably injure the vessel in which it was supposed to be introduced if it were pushed. Also, the shape of the endoprosthesis would be affected by this forcing action; it would be compressed and its supporting elements would buckle.

If it is discovered when the endoprosthesis is released and unfolded that the final location does not correspond to the desired position, the possibility should thus exist of pulling the endoprosthesis back into the device again after it is partially released so that it can accordingly be repositioned in a folded state.

A device of this type, described as an instrument for inserting a self-expanding implant, is outlined in [design patent] DE-GBM G 90 10 130.8. This device consists basically of an outer casing inside of which is an axial hollow core. The core has a diameter that increases incrementally at its distal end, whereby the distal end of the core strikes against the distal end of the casing. Around the distal end of the core is a gripping component that firmly holds a self-expanding implant in such a way that it can be separated. In order to produce a friction-locking connection between the core or the gripping component and the expanding prosthesis, the gripping component is made of a high-friction material. In addition, another type model provides for coating the gripping component with an agent for gluing the expanding implant in such a way that it can be separated.

A disadvantage of this device is the fact that the outer casing must tightly enclose the expanding implant so that a friction-locking connection is ensured between the gripping component and the self-expanding implant as proposed. As a result of this, a relative displacement creates a great deal of friction between the core and the outer casing, and naturally between the expanding implant and the inner wall of the outer casing, so that consequently forces exerted to release the expanding implant and to withdraw it are great. Furthermore, there is a risk that due to the relatively strong forces being exerted, reliability with respect to precise positioning of the implant will be adversely affected accordingly, because in addition to the friction between the expanding implant and the outer casing, there is also the friction between the core and the outer casing along the entire remaining length of the device. Moreover, it is more expensive to ensure by creation of the corresponding friction coefficients that the relative movement actually occurs as intended between the expanding implant and the outer casing, although there the normal force on the friction surfaces is higher by the total expansion force of the expanding implant than the normal force between the core and expanding implant.

With this device it is crucial, in order to achieve a very specific friction between the core and the expanding implant, that a normal force also be required that is just as precise. In this case, the amount of normal force is determined by the elasticity of the outer casing, the elasticity of the expanding implant, and the elasticity of the core, on the one hand, and by the inner diameter of the outer casing, the thickness of the expanding implant and the outer diameter of the core, on the other. Moreover, the expansion force of the expanding implant further determines the amount of normal force; it works against the normal force. The required normal force must be met exactly in order to produce a specific friction force; on the other hand, however, the normal force is very sensitive to the determining factors cited. Mass production of this device therefore presents great problems.

The additional proposal in the aforementioned design patent with respect to coating the gripping component with an agent for gluing the expanding implant in such a way that it can be separated brings with it the risk that the expanding implant, especially when stored for longer periods, will no longer expand on its own after the outer casing is pulled back, since its opening force is too weak, or that the adhesive coat will undergo chemical changes with time and consequently that the desired friction-locking connection will no longer be guaranteed. Applying the adhesive coat also presents problems; every effort must be made to prevent the adhesive coat from getting between elements of the expanding implant, which must move toward one another when the implant expands. Separable adhesive agents derive their properties from the fact that they always retain certain rheological properties; they do not harden. Consequently, the danger exists that adhesive agents that are properly applied originally will begin to run during the time the device is stored and that the expanding implant will become stuck together.

Another type model of the design patent provides for supplying the gripping component with a roughened surface. However, with a roughened surface, there is the danger that the expanding implant will become deformed and, as a result, that its shape will be affected, particularly when it expands.

It should be noted in general that a sure method of operation cannot be achieved in every case by means of type models such as those proposed in the aforementioned design patent, since with the manufacturing of expanding implants and, in particular, with the type of compression, high tolerances with respect to accuracy to gauge and expansion force must be reckoned with.

SUMMARY OF THE INVENTION

It is therefore the purpose of the invention to provide a simple device for implanting endoprostheses and folding them back up again in which, compared to devices that do not permit the endoprosthesis to be folded back up again, the operating force is not increased and the free and undeformed unfolding of the endoprosthesis is not affected, which can be manufactured easily and inexpensively, which guarantees sure operation even after long storage periods, and in which even certain unavoidable manufacturing tolerances of the endoprosthesis do not have any adverse affect on its sure operation, particularly in releasing the endoprosthesis and folding it back up again.

Another purpose of the invention consists of providing a process for impressing a stamping on this device and for doing so easily.

Designing the endoprosthesis in such a way that the core element exhibits on a portion of its surface an impressed relief that corresponds to the structure of the inner surface of the endoprosthesis guarantees, on the one hand, that the forces exerted to move the core element in relation to the outer body can be kept to a minimum and, on the other hand, that a sure radial separation of the self-expanding endoprosthesis from the core element is still ensured even after a long storage period. Thus sure and reliable operation is achieved by means of such a design. This type of endoprosthesis can also be manufactured easily and inexpensively.

A preferred type model of the invention provides for the relief impressed on the core element to be individually adapted to the structure of the inner surface of the endoprosthesis. Such a design ensures that an optimal form-locking connection is achieved between the core element and the endoprosthesis and therefore guarantees the greatest possible operational reliability. In this case, the individual form-locking meshing sites are individually matched to one another with respect to their position, arrangement, and design.

A preferred process provides for using the individual endoprosthesis that is to be inserted in the device to form the relief. An advantage of this process is that great tolerances with respect to accuracy to gauge of the endoprosthesis do not themselves adversely affect the operational reliability of the device.

BRIEF DESCRIPTION OF THE DRAWINGS

Two examples of the invention's design are explained in greater detail in the following using the drawings. The drawings show:

FIG. 1. A device in a partial cutaway view with a separate representation of a folded endoprosthesis;

FIG. 2. The device in partial cutaway view with an enclosed endoprosthesis;

DETAILED DESCRIPTION OF THE INVENTION

Figure 3A:
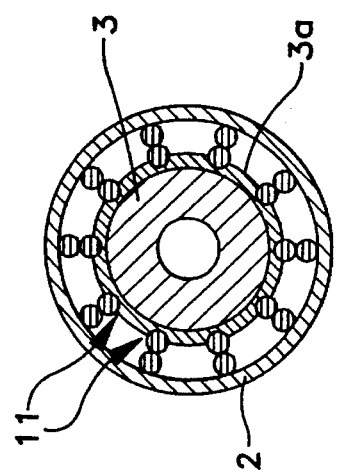
FIG. 3a An enlarged cross section through a second type model of the device along line A—A in FIG. 2.

The device represented in FIG. 1 for implanting endoprosthesis 1 has basically a tubular, flexible outer body 2 and an elongated, flexible core element 3.

Tubular outer body 2 is represented in lengthwise section from break line x to its distal end. At its proximal end, tubular body 2 is provided with a handle 5. Elongated core element 3 is placed in tubular body 2, where core element 3 is designed to be longer than tubular body 2 and also has a handle 6. Toward its distal end, core element 3 exhibits a region B, which serves to receive endoprosthesis 1. This region B exhibits at its proximal end a shoulder 8 made from X-ray opaque material. Distally contiguous to this is a section 9, the diameter of which is reduced. Following section 9 is an area 10 in which a relief in the form of a stamping 11 is impressed and which exhibits a somewhat larger diameter than section 9 preceding it. The form of relief or stamping 11 corresponds to the structure of the inner surface of folded endoprosthesis 1. Contiguous to area 10 lies a section 13 that exhibits approximately the same diameter as section 9. Following this is a ring 14, which is also made of X-ray opaque material and which is designed to be somewhat larger in diameter than section 13. Finally, at its distal end, core element 3 has a blunt, cone-shaped tip 15.

Extending the entire length of core element 3 is a lumen 16 in which a guide wire 17 can be inserted. For the sake of better clarity, endoprosthesis 1 is depicted outside of the device and folded up in this representation. In this way, the correlation between the form of stamping 11 and that of folded endoprosthesis 1 can be seen. It can also be clearly seen from this representation that the length of area 10, which is provided with stamping 11, is shorter than the length of the endoprosthesis; it preferably totals approximately 10–50% of the length of the endoprosthesis. As a result of this length of stamping 11, the flexibility of the device in region B of endoprosthesis 1 is affected as little as possible by the piled up material and the form locking in the stamping area. On the other hand, however, a reliable form-locking connection between enclosed endoprosthesis 1 and core element 2 is guaranteed.

FIG. 2 shows the device in a ready-to-use condition. Here endoprosthesis 1 is enclosed folded up between core element 3 and tubular outer body 2. At the same time, the inner surface of endoprosthesis 1 meshes with core element 3 along stamping 11 impressed in area 10. Stamping 11 corresponds to the structure of the inner surface of endoprosthesis 1, so that a large number of form-locking meshing sites are formed between area 10 of core element 3 and endoprosthesis 1. Since the individual threads of a layer of endoprosthesis 1 diverge when the latter is folded up, differences in the location of the threads with respect to stamping 11 could result in the region of the proximal and distal ends of endoprosthesis 1. For this reason, it is advantageous to provide sections 9 and 13, which have a smaller diameter than area 10, between the latter, which is provided with stamping 11, and the ends of endoprosthesis 1.

Figure 3:
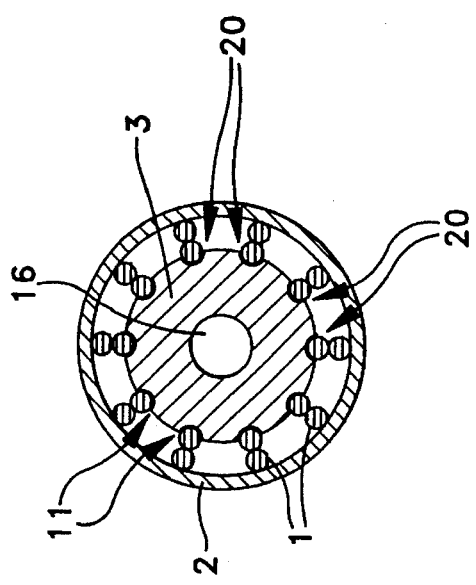
FIG. 3. An enlarged cross section through a first type model of the device along line A—A in FIG. 2.

A first type model of the device can be seen in FIG. 3 in an enlarged cross section along line A—A of FIG. 2. Endoprosthesis 1 is enclosed between tubular outer body 2 and core element 3. The distance between the outer diameter of core element 3 and the inner diameter of tubular outer body 2 is chosen in such a way that the inner layer of endoprosthesis 1 is pressed into the recesses resulting from stamping 11. The depth of stamping 11 corresponds to approximately 50% of the thickness of the inner layer of the semifinished material used in endoprosthesis 1. In this case, a thin wire is used as the semifinished material for manufacturing endoprosthesis 1. However, the same ratio applies if endoprosthesis 1 is punched out, for example, from thin sheet metal or is made of strip metal. The above-mentioned depth of stamping 11 ensures a good form-locking connection between core element 3 and endoprosthesis 1 by means of a large number of form-locking meshing sites 20 and guarantees, in addition, sure radial separation and unfolding of released endoprosthesis 1, because the form-locking connection does not affect the relative motion of the layers of semifinished material in relation to one another.

A second type model of the device is illustrated in FIG. 3a in an enlarged cross section along line A—A in FIG. 2. In this example, core element 3 has a coating or sheath 3a. The advantage of such a coating or sheath 3a is that it can exhibit properties other than those of core element 3. The change in diameter required in this area can be easily obtained as well by means of this sheath or coating 3a. Thus, for example, the thermoplasticity of core element 3 can be lower than that of coating or sheath 3a. Consequently, the depth of stamping 11 can be easily influenced by the thickness of coating or sheath 3a. Sheath 3a can be manufactured very easily, for example, by shrinking a contracting tube onto core element 3.

Figure 4:
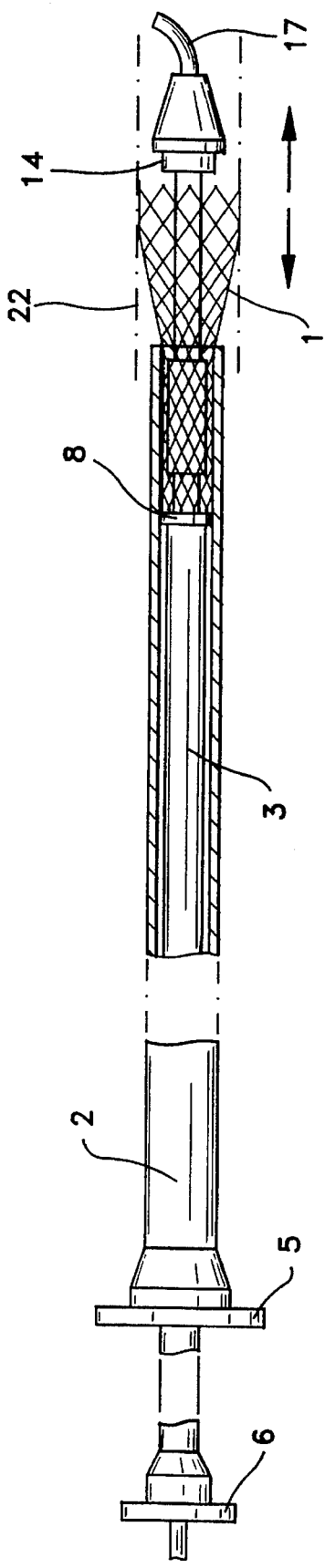
FIG. 4 The device in a partial cutaway view with a partially unfolded endoprosthesis.

The operation of the device is explained by means of FIG. 4. Using the device, endoprosthesis 1 is inserted folded (FIG. 2) in a body canal 22, which is only indicated schematically, in the known manner and is advanced until the distal end region B of the device is positioned so that enclosed endoprosthesis 1 is at the desired location in body canal 22. At the same time, the advance of folded endoprosthesis 1 in body canal 22 is monitored by means of known processes such as fluoroscopy. The location of endoprosthesis 1 is readily visible due to X-ray opaque rings 8 and 14, which are fitted on core element 3 in the area of the two ends of enclosed endoprosthesis 1.

Once endoprosthesis 1 is in the intended final position, core element 3 is locked into position and endoprosthesis 1 is slowly released by pulling back tubular outer body 2. The two handles 5 and 6 are used for this purpose. Since endoprosthesis 1 is self-expanding, the released portion begins to unfold and rest against the inner wall of body canal 22. In unfolding, the length of endoprosthesis 1 is shortened accordingly. Since there is a direct connection between the shortening of endoprosthesis 1 and the inner diameter of body canal and the diameter of endoprosthesis 1 in its inserted, unfolded state but the final amount of expansion is not known exactly, the final position of unfolded endoprosthesis 1 cannot be determined with certainty beforehand. Thus the position of endoprosthesis 1 must also be monitored during the unfolding. If monitoring shows that it is positioned correctly, endoprosthesis 1 can be completely released by pulling back tubular body 2 to the area of shoulder 8 of core element 3. If, however, it is discovered during the unfolding that endoprosthesis 1 is not in the correct position, it can be folded back up again in tubular body 2 by moving tubular body 2 forward. This makes it possible for endoprosthesis 1 to then be repositioned accordingly and released again in the new position in the manner described above.

By means of a form-locking connection between endoprosthesis 1 and core element 3, which is achieved via stamping 11, which corresponds to the structure of the inner surface of endoprosthesis 1, and via endoprosthesis 1, which meshes with stamping 11, it can be ensured, on the one hand, that the forces exerted to move core element 3 with respect to outer body 2 can be kept to a minimum and, on the other hand, that sure radial separation of self-expanding endoprosthesis 1 from core element 3 is still guaranteed even after a long period of storage. In short, sure and reliable operation is achieved by way of a device with this design. It can also be manufactured easily and inexpensively.

The process for producing a stamping for this type of device can go as follows: An endoprosthesis 1 is pushed unfolded onto region B of core element 3. Then endoprosthesis 1 is folded up in the area of section 9 of core element 3 in which there is no stamping. Next, tubular outer body 2 is pushed forward up to the proximal end of area 10 of core element 3. Endoprosthesis 1 is secured in position in this way. Endoprosthesis 1 is subsequently folded up in the area where it is exposed by a pressing die, which is in itself known, and pressed by the pressing die on area 10 of core element 3. The pressing die is now warmed with hot air so that endoprosthesis 1, which has been pressed together, is heated and in this way pressed into the thermoplastic material of core element 3 or into its coating or sheath 3a. After removing the pressing die, tubular outer body 2 is pushed forward until its distal end lies against the back side of tip 15 of core element 3 and endoprosthesis 1 is thus completely enclosed. A corresponding process is utilized if a hardened plastic is used instead of the thermoplastic material. While this process is being carried out, it is absolutely imperative that shoulder 8 does not rest against the proximal end of endoprosthesis 1. It automatically rests against the proximal end of endoprosthesis 1 once endoprosthesis 1 comes unmeshed from core element 3 upon release. Shoulder 8 serves then as an abutment for endoprosthesis 1 when the remaining portion of the endoprosthesis still enclosed in tubular body 2 is released.

Obviously, processes are also conceivable in which the same endoprosthesis is always used to form the stamping. Furthermore, it is also possible to impress the stamping by means of a positive cast of an endoprosthesis formed on the pressing die.

I claim:

1. An implanting device in combination with a tubular radially self-expanding endoprosthesis comprising: an elongated inner core element having an outer surface over which said endoprosthesis is placed and a tubular outer body that can be moved in relation to said core element and that at least partially surrounds said core element and said endoprosthesis to hold said endoprosthesis in a radially contracted state, the endoprosthesis having a longitudinal length in a radially contracted state, wherein said core element has a stamping on its outer surface corresponding to at least 10% and at most 50% of the longitudinal length of the contracted endoprosthesis, the stamping essentially complementing the shape of an inner surface of said endoprosthesis when said endoprosthesis is in a radially contracted state.

2. The device according to claim 1, wherein said implanting device is configured to be used to implant various endoprostheses, wherein said stamping is individually adapted to complement the structure of the inner surface of each endoprosthesis used.

3. The device according to claim 1, wherein said endoprosthesis has a proximal end and said core element has an area that has no stamping at the proximal end of the endoprosthesis.

4. The device according to claim 1, wherein a depth of said stamping is at least approximately 50% of a thickness of the endoprosthesis.

5. The device according to claim 1, wherein an average distance between an outer diameter of said core element and an inner diameter of said tubular body is less than a thickness of the endoprosthesis in a region of said stamping.

6. The device according to claim 1, wherein said core element has a lumen for receiving a guide wire.

7. The device according to claim 1, wherein said core element has a shoulder situated proximally with respect to the endoprosthesis.

8. The device according to claim 1, wherein said core element has an outer surface in regions bordering said stamping that do not have any stamping.

9. An implanting device in combination with a tubular radially self-expanding endoprosthesis comprising: an elongated inner core element having a distal end and an outer surface over which said endoprosthesis is placed and a tubular outer body that can be moved in relation to said core element and that at least partially surrounds said core element and said endoprosthesis to hold said endoprosthesis in a radially contracted state, wherein said core element has a coating or sheath at least in a region of the distal end having a stamping essentially complementing an inner surface of said endoprosthesis when said endoprosthesis is in a radially contracted state.

10. The device according to claim 9, wherein said coating or sheath is made of a thermoplastic material.

11. The device according to claim 10, wherein said coating or sheath is a sheath comprising a piece of plastic tubing which is shrunk onto said core element.

12. The device according to claim 9, wherein the core element has a thermoplasticity which is lower than a thermoplasticity of the coating or sheath.

13. An implanting device in combination with a tubular radially self-expanding endoprosthesis comprising: an elongated inner core element having an outer surface over which said endoprosthesis is placed and a tubular outer body that can be moved in relation to said core element and that at least partially surrounds said core element and said endoprosthesis to hold said endoprosthesis in a radially contracted state, wherein said core element, at least on part of its outer surface, has a stamping essentially complementing the shape of an inner surface of said endoprosthesis when said endoprosthesis is in a radially contracted state and wherein the endoprosthesis comprises several layers and at most 50% of a thickness of an innermost layer of the endoprosthesis meshes with said stamping.

14. An implanting device in combination with a tubular radially self-expanding endoprosthesis comprising: an elongated inner core element having an outer surface over which said endoprosthesis is placed and a tubular outer body that can be moved in relation to said core element and that at least partially surrounds said core element and said endoprosthesis to hold said endoprosthesis in a radially contracted state, wherein said core element, at least on part of its outer surface, has a stamping essentially complementing the shape of an inner surface of said endoprosthesis when said endoprosthesis is in a radially contracted state, wherein said core element has a shoulder situated proximally with respect to the endoprosthesis and the shoulder comprises a ring made of x-ray opaque material.

* * * * *